United States Patent [19]
Oneda et al.

[11] Patent Number: 5,827,177
[45] Date of Patent: Oct. 27, 1998

[54] ENDOSCOPE SHEATH ASSEMBLY WITH ISOLATING FABRIC SLEEVE

[75] Inventors: Katsumi Oneda, Alpine, N.J.; E. Paul Harhen, Duxbury, Mass.

[73] Assignee: Vision-Sciences, Inc., Natick, Mass.

[21] Appl. No.: 801,744

[22] Filed: Feb. 18, 1997

[51] Int. Cl.$^6$ .......................................... A61B 1/04
[52] U.S. Cl. ........................ 600/121; 600/123; 600/153
[58] Field of Search ................................. 600/121, 122, 600/123, 124, 125, 146, 147, 148, 149, 150, 151, 152, 153, 156, 157, 158, 159, 161

[56] References Cited

U.S. PATENT DOCUMENTS

| Re. 34,110 | 10/1992 | Opie et al. ................................ 128/6 |
| 3,794,091 | 2/1974 | Ersek et al. ........................... 150/52 R |
| 3,809,072 | 5/1974 | Ersek et al. ............................... 128/23 |
| 4,646,722 | 3/1987 | Silverstein et al. ........................ 128/4 |
| 5,019,042 | 5/1991 | Sahota ..................................... 604/101 |
| 5,271,381 | 12/1993 | Ailinger et al. ............................. 128/4 |
| 5,483,951 | 1/1996 | Frassica et al. .......................... 600/104 |

*Primary Examiner*—Beverly M. Flanagan
*Attorney, Agent, or Firm*—Seed and Berry LLP

[57] ABSTRACT

An endoscope sheath assembly usable within an elongated flexible endoscope to isolate a portion of the endoscope from an external environment during a therapeutic or diagnostic endoscopic procedure. The sheath assembly has a sheath with an elongated flexible endoscope tube, a plurality of working channels extending the endoscope tube, and a low-friction, fabric isolating sleeve positioned within the endoscope tube and surrounding portions of the working channels. The isolating sleeve includes first and second sleeve lumens formed therein through which respective working channels extend. The coefficient of friction between the isolating sleeve and the working channels is less than the coefficient of friction between the working channels themselves so that working channels are frictionally isolated from each other, from the endoscope tube, and from the insertion tube to reduce resistance to articulation of the endoscope.

29 Claims, 4 Drawing Sheets

ENDOSCOPE SHEATH ASSEMBLY WITH ISOLATING FABRIC SLEEVE

TECHNICAL FIELD

The present invention is directed toward the field of endoscopy, and more particularly, to endoscope isolation assemblies having working channels therein.

BACKGROUND OF THE INVENTION

The use of endoscopes for diagnostic and therapeutic indications is rapidly expanding. To improve performance, endoscopes have been optimized to best accomplish their purpose. Therefore, there are upper endoscopes for examination of esophagus, stomach, and duodenum; colonoscopes for examining the colon; angioscopes for examining blood vessels; bronchoscopes for examining the bronchii; laparoscopes for examining the periotonital cavity; and arthroscopes for examining joint spaces. The discussion which follows will apply to all of these types of endoscopes.

Instruments to examine the rectum and sigmoid colon, known as flexible sigmoidoscopes, are good examples of the usefulness of the endoscopic technology. These devices are expensive, and they are used in a contaminated environment for a brief procedure (5–10 minutes) to screen symptomatic and asymptomatic patients for colon and rectal cancer. Typically, these endoscopes have a flexible insertion tube that is inserted into a patient during an endoscopic procedure. During insertion, the position of the distal end of the insertion tube is controlled by control devices on the endoscope's handle at the proximal end of the insertion tube. The distal end of the insertion tube must be sufficiently flexible to bend through tight radius corners during insertion.

Conventional non-sheathed endoscope assemblies have multiple, internal working channels that extend through the interior of the insertion tube and terminate at the insertion tube's distal end. The working channels allow air insufflation into a body cavity, water flow to wash the insertion tube's tip, suction through the tip, and biopsies to be taken. The channels must bend without kinking as the insertion tube is articulated through short radius turns to assure continuous airflow, water flow, suction, and biopsy capabilities throughout an endoscopic procedure.

The working channels come into contact with body tissues and fluids during an endoscope procedure, so the working channels are severely contaminated after the procedure. The insertion tube and the working channels must be cleaned and sterilized before being used in a subsequent procedure. This cleaning and sterilization is very laborious and costly, thereby reducing the cost effectiveness of performing the therapeutic or diagnostic endoscopic procedures.

Endoscopes and disposable endoscopic sheath assemblies have been developed to alleviate the problem of cleaning and sterilizing the work channels. As best seen in FIG. 1, a conventional endoscope 10, such as is disclosed in U.S. Pat. Nos. Re. 34,110 and 5,271,381, has an insertion tube 12 that is connected at its proximal end 14 to a control body 16 of the endoscope. The insertion tube 12 is asymmetric and has a D-shaped cross-section with a flat top surface and a curved bottom surface.

The insertion tube 12 has an imaging device 18 extending through it along its length, and the imaging device terminates at a viewing window in the distal end 20 of the insertion tube. The imaging device 18 conveys an image from the distal end 20 of the insertion tube 12 to an eyepiece 22 on the control body 16 or to a monitor (not shown), so the user can see into the selected body cavity during the endoscopic procedure. The imaging device 18 must be sufficiently flexible to allow the insertion tube 12 to bend without excessive resistance as the distal end 20 of the insertion tube is moved and positioned within the body cavity.

The position of the insertion tube's distal end 20 is controlled by control wires (not shown) that extend through the insertion tube. The control wires are connected at one end to the insertion tube's distal end 20 and are connected at an opposite end to control wheels 24 mounted to the control body 16. The control wires allow the user to move the distal end 20 of the insertion tube 12 left, right, up, down, and any combination thereof. Rotation of the control wheels 24 moves the control wires axially, causing a distal articulating section of the insertion tube 12 to bend about a neutral bending plane extending through the insertion tube, so the distal end 20 of the insertion tube can be directed around tight radius corners.

The insertion tube 12 is sized to extend into a sheath assembly 28 shown in FIG. 2A. The sheath assembly 28 has a sheath 29 with a thin-walled, flexible endoscope tube 30 that fits over and tightly surrounds the asymmetric insertion tube 12, shown in phantom lines, to isolate the insertion tube from an external environment during the procedure. The endoscope tube 30 has a substantially circular cross-section, so the D-shaped insertion tube 12 fills approximately half of the endoscope tube with the curved surface of the insertion tube engaging the axial walls of the endoscope tube.

The sheath assembly 28 also includes elastomeric working channels 32 that extend through the endoscope tube 30 and connect to a distal end of the sheath 29. The working channels 32 typically include a biopsy/suction channel that is coupled to a suction source (not shown), a water channel connected to a water source (not shown), and an air channel connected to an air source (not shown). As best seen in FIG. 2B, the working channels 32 are positioned next to the flat surface of the insertion tube 12 when the insertion tube is positioned in the endoscope tube 30. Accordingly, the other half of the endoscope tube 30 above the flat surface of the insertion tube 12 is substantially filled by the working channels 32.

When the insertion tube 12 is inserted into the sheath assembly 10, the working channels 32 are spaced apart from the neutral bending plane of the insertion tube. As the insertion tube 12 is articulated, the elastomeric working channels 32 are also articulated and they stretch or compress in order to follow the curvature of the bent insertion tube. For example, when the insertion tube 12 is articulated to move the distal end 20 downwardly, when viewed in FIGS. 2A and B, the working channels 32 are extended and stretched along the flat surface of the insertion tube, and when the distal end is moved upwardly, the working channels are compressed.

The working channels 32 resist being compressed or stretched during articulation of the insertion tube 12. This resistance adversely impacts the control, sensitivity, feel, and other handling characteristics of the sheathed insertion tube. The sheathed insertion tube is more difficult to articulate in some directions and easier to articulate in other directions. Because the working channels are off-axis from the neutral bending plane, this resistance to articulation of the insertion tube 12 can result in fatigue to the user manipulating the control wheels 24 (FIG. 1), particularly during a long endoscopic procedure.

The handling characteristics of conventional sheathed endoscopes are also adversely impacted by friction that occurs along the working channels. More particularly, the working channels 32 are tightly surrounded by the endoscope tube 30 when the insertion tube 12 is inserted into the sheath 29, and the endoscope tube presses the working channels against each other and against the flat surface of the insertion tube. Friction between the individual working channels 32 and friction between the insertion tube 12 and the working channels results in resistance to the working channels 32 being stretched, compressed or otherwise moved axially during articulation of the insertion tube. This frictional resistance requires the user to work harder to articulate the insertion tube.

A further drawback to the conventional sheath assembly is that the working channels are susceptible to being tangled or misaligned within the endoscope tube when the insertion tube is being installed or during an endoscopic procedure. The working channels in some conventional sheath assemblies are glued or taped to each other at close intervals to prevent misalignment during installation and operation of the endoscope. Other conventional sheath assemblies use conformable tape material applied along substantially the lengths of the working channels to prevent twisting and endoscope misalignment. However, the glued or taped working channels are held together as a bundle of channels pressed against each other, which results in surface friction that causes one working channel to constrain movement of an adjacent working channel. A further disadvantage of the bundle of taped or glued working channels is that the manufacturing processes are too laborious to be cost effective in the design of a disposable medical product.

SUMMARY OF THE INVENTION

The present invention is directed toward an endoscopic sheath assembly that overcomes the drawbacks experienced by the conventional assemblies. One embodiment of the present invention provides an endoscope sheath assembly having a sheath with an endoscope tube adapted to isolate at least a portion of an endoscope insertion tube from an external environment. Working channels extend through the endoscope tube and terminate adjacent to a distal end of the endoscope tube. An isolating sleeve is contained within the endoscope tube and has lumens that receive and surround portions of the working channels so as to isolate the portions of the first and second working channels from each other, from the endoscope tube, and from an insertion tube of an endoscope when the sheath is installed on an endoscope.

In one embodiment of the invention, a distal portion of a first working channel extends through a first lumen of the isolating sleeve and a distal portion of a second working channel extends through a second lumen of the isolating sleeve, such that the distal portions of the first and second working channels are axially movable within the respective lumens relative to each other and relative to the insertion tube upon articulation of the insertion tube.

In the preferred embodiment, the isolating sleeve is a stretchable, sheer fabric material, and the coefficient of friction between fabric material and the first or second working channel is less than the coefficient of friction between the first and second working channels. Accordingly, the isolating sleeve reduces frictional resistance to articulation of the insertion tube, and the distal portions of the first and second working channels are frictionally isolated from each other.

In an alternative embodiment of the invention, the isolating sleeve is constructed of a low-friction, sheer fabric that is substantially nonstretchable. The nonstretchable isolating sleeve has a selected length that is longer than the portions of the working channels extending therethrough when the insertion tube is nonarticulated position. When the endoscope insertion tube is articulated in one direction, the nonstretchable isolating sleeve is pulled toward its full length, and when the insertion tube is articulated in the opposite direction, the nonstretchable sleeve is bunched without restricting articulation of the insertion tube.

The present invention is also directed toward a method of isolating working channels of an endoscopic sheath assembly from an insertion tube of an endoscope. The method includes the steps of positioning first and second working channels within an endoscope tube of an endoscopic sheath assembly, enclosing a distal portion of a first working channel in a lumen of a first sleeve portion isolating the first working channel from the endoscope tube, and enclosing a distal portion of the second working channel in a lumen of a second sleeve portion with the second sleeve portion isolating the distal portion of the second working channel from the endoscope tube and the first working channel.

The present invention is also directed toward a method of articulating an endoscope insertion tube and a sheath assembly. The method includes the steps of inserting the insertion tube into an endoscope tube of the sheath assembly, enclosing distal portions of first and second working channels in respective first and second sleeve portions to isolate the distal portions from each other, from the endoscope tube and from the insertion tube and articulating the insertion tube, about a neutral bending plane that is spaced apart from the first and second working channels.

DETAILED DESCRIPTION OF THE INVENTION

Figure 1:
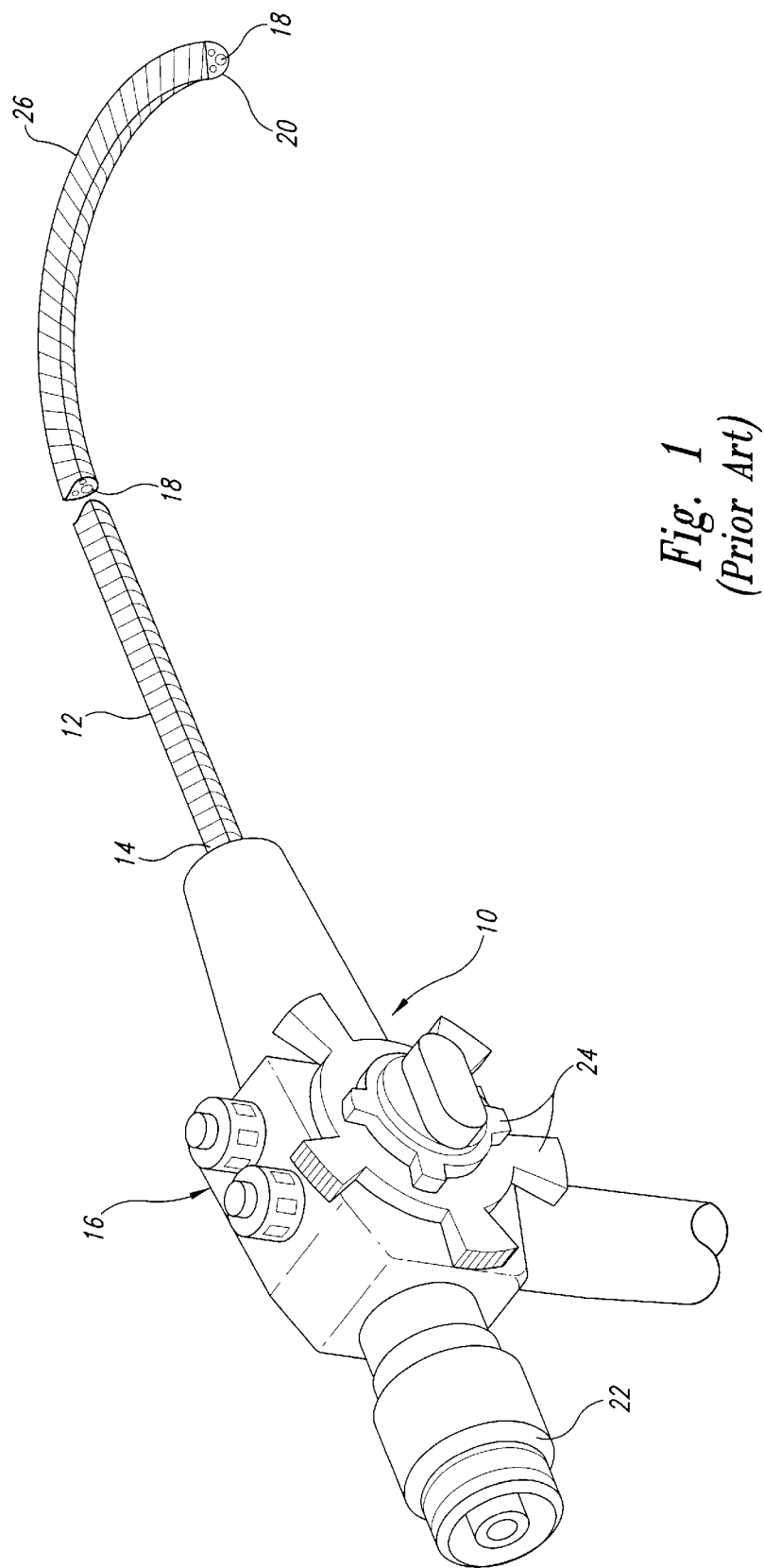
FIG. 1 is an isometric view of a conventional, prior art endoscope that is usable with a sheath assembly (not shown).
Figure 2A:
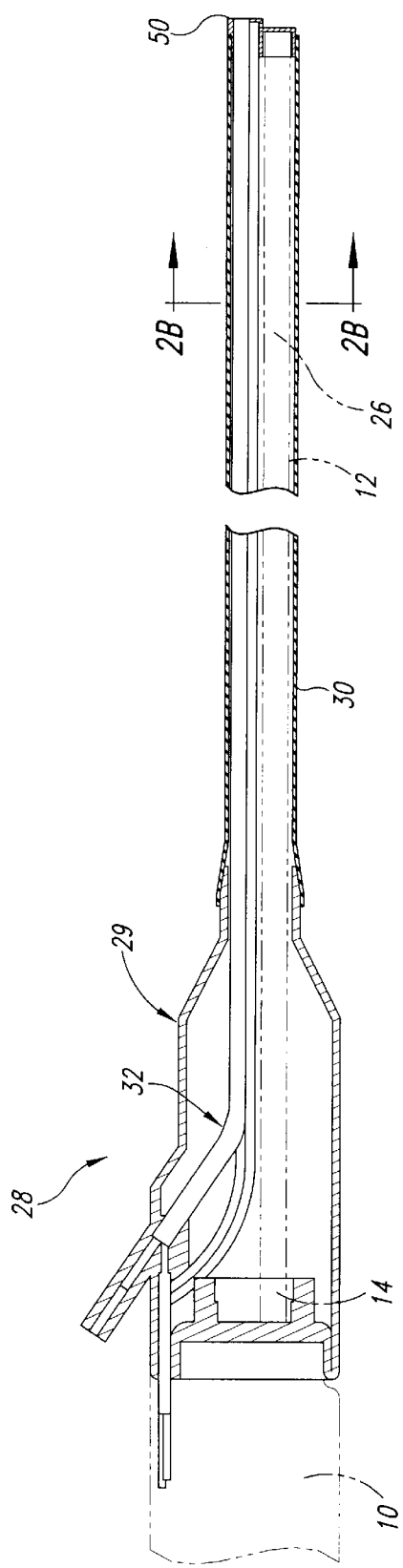
FIG. 2A is a cross-sectional view of a conventional, prior art endoscopic sheath assembly that removably receives the endoscope insertion tube of FIG. 1, shown in phantom lines.
Figure 2B:
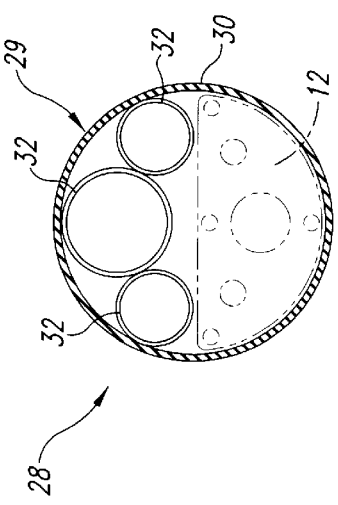
FIG. 2B is an enlarged cross-sectional view taken substantially along line 2B—2B of FIG. 2A showing the conventional prior art sheath assembly with working channels contained within an endoscope tube and positioned adjacent to the insertion tube, the insertion tube being shown in phantom lines.
Figure 3:
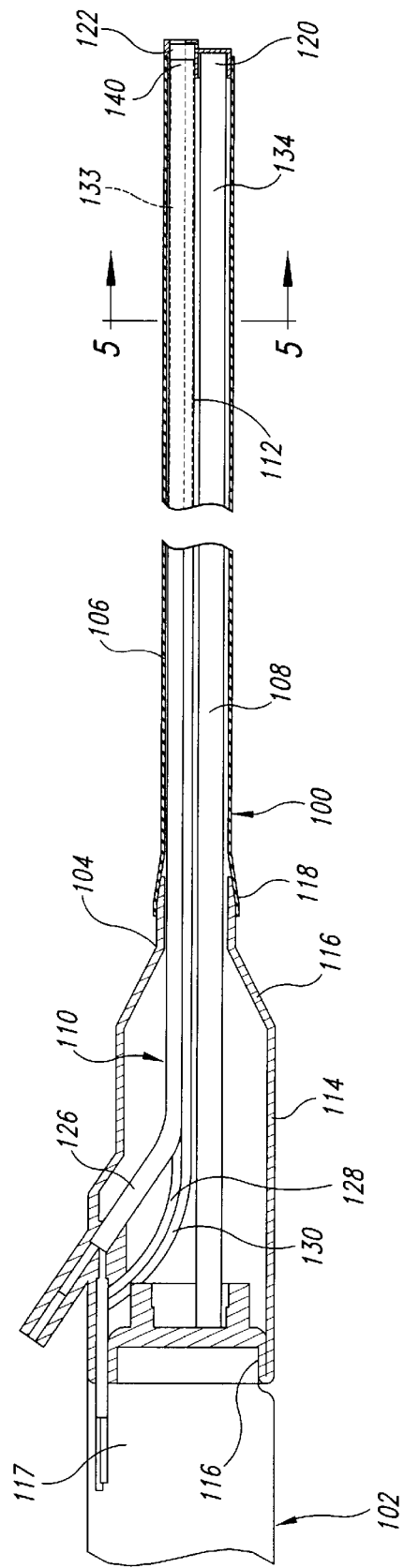
FIG. 3 is a cross-sectional view of a sheath assembly in accordance with a preferred embodiment of the present invention, the sheath assembly having working channels extending through a sheath and through a low-friction isolating sleeve, and the sheath being shown covering an endoscope insertion tube.

Embodiments of the present invention described herein are shown in FIGS. 3–6. As best seen in FIG. 3, a protective sheath assembly 100 is adapted for use with an endoscope 102 during a therapeutic or diagnostic endoscopic procedure to isolate at least a portion of the endoscope from an external environment during the procedure. The sheath assembly 100 has a sheath 104 with a thin-walled, flexible endoscope tube 106 that fits over and tightly surrounds an insertion tube 108 of the endoscope 102. The endoscope tube 106 has a substantially circular cross-section and it receives the insertion tube 108, which has a D-shaped cross-section. Accordingly, the insertion tube 108 fills approximately half of the endoscope tube 106, with the curved side of the insertion tube engaging axial walls of the endoscope tube.

The sheath assembly 100 includes a plurality of working channels 110 that extend through the endoscope tube 106 and connect to a distal end 107 of the sheath 104. When the sheath assembly 100 is installed on the endoscope 102, the working channels 110 extend axially next to the insertion tube 108, and upon articulation of the insertion tube during the endoscopic procedure, the working channels bend with the insertion tube.

Referring to the sheath 104 shown in FIG. 3, the sheath has a rigid plastic connecting member 114 that receives the insertion tube 108 through an open proximal end 116, and the open proximal end releasably attaches to a control body 117 of the endoscope 102. The distal end of the connecting member 114 is sealably attached to a proximal end 118 of the endoscope tube 106.

The sheath 104 also has an end cap 120 at its distal end that is sealatily connected to the distal end of the endoscope tube 106 to prevent bodily fluids or other contaminants from entering the endoscope tube and contaminating the insertion tube 108. The end cap 120 also removably attaches to the distal end of the insertion tube 108 to align a viewing window (not shown) in the end cap with the imaging device (not shown) in the endoscope's insertion tube 108.

The working channels 110 sealably connect at open distal ends to the end cap 120 and extend proximally through the endoscope tube 106. The working channels 110 are positioned between the axial wall of the endoscope tube 106 and the flat surface of the insertion tube 108, such that the working channels substantially fill the other half of the endoscope tube. When the sheath assembly 100 is installed on the endoscope 102, the endoscope tube 106 is stretched over and tightly surrounds the working channels 110.

In the preferred embodiment, the working channels 110 include a biopsy channel 126, a water channel 128, and an air channel 130 that each extend into and connect to the sheath's connecting member 114. The biopsy channel 126 is a kink-resistant elastomeric tube that is shaped and sized to allow endoscopic accessories to extend through the channel and through the end cap 120 into a body cavity during an endoscopic procedure. The biopsy channel 126 is coupled at its proximal end to a suction line 132 in the connecting member 114 that is connectable to a remote suction source (not shown) so the biopsy channel acts as a biopsy/suction channel. However, the biopsy channel 126 can also be used solely as a biopsy channel with the suction being provided through a different working channel.

The water channel 128 and the air channel 130 are each attached at distal ends to respective air and water distribution nozzles formed in the end cap 120. The nozzles are directed toward the viewing window in the end cap 120 to direct air or water over the viewing window to keep the viewing window clear during an endoscopic procedure. Proximal ends of the water and air channels 128 and 130 are connectable to respective water and air sources (not shown).

When the sheath assembly 100 is installed on the endoscope 102, distal portions 133 of the working channels 110 are positioned adjacent to an articulating section 134 of the endoscope's insertion tube 108. This articulating section 134 has a high degree of flexibility that allows the insertion tube 108 and the distal portions 133 of the working channels 110 to be bent around tight radius corners for ease of positioning and controlling the endoscope's insertion tube during an endoscopic procedure.

The sheath assembly 100 also has a low-friction isolating sleeve 112 located within the endoscope tube 106, and the isolating sleeve surrounds the distal portions 133 of the working channels 110 adjacent to the articulating section 134. The isolating sleeve 112 isolates the distal portions 133 of the working channels 110 from each other, from the insertion tube 108, and also from the endoscope tube 106 to reduce resistance to articulation of the insertion tube.

The isolating sleeve 112 has a distal end 140 securely connected to the end cap 120 and a proximal end 142 securely attached to the working channels 114 at an intermediate position between the proximal and distal ends of the working channels. The proximal end 142 of the isolating sleeve 112 has a reinforced portion 154 located proximal to the articulating section 134 of the insertion tube. The reinforced portion 154 is adhered to the working channels 110 to prevent the isolating sleeve from sliding distally during articulation of the insertion tube 108 or during installation of the insertion tube. This reinforced portion 154 also prevents the proximal end 142 of the isolating sleeve 112 from inadvertently unraveling or disconnecting during installation or articulation of the insertion tube 108.

Figure 4:
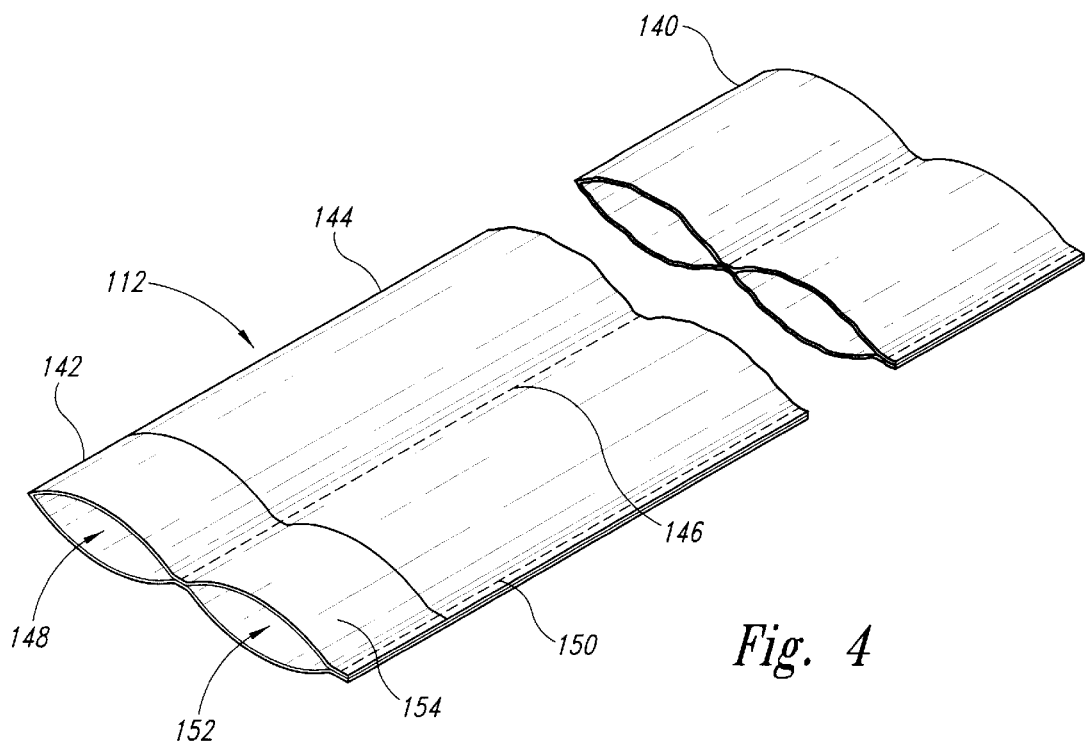
FIG. 4 is an enlarged isometric view of the isolating sleeve of FIG. 3, the isolating sleeve being shown removed from the sheath.

As best seen in FIG. 4, the isolating sleeve 112 of the preferred embodiment has a first lumen 148 formed by a sheet of sheer, low-friction fabric material that is folded over at 144 and stitched to itself with a first longitudinal line of stitching 146. A second lumen 152 is formed by a second longitudinal line of stitching 150 that joins the edges of the material to each other at a position spaced away from the first line of stitching 146. The first and second lumens 148 and 152 are each open at the isolating sleeve's distal end 140 and proximal end 142.

Figure 5:
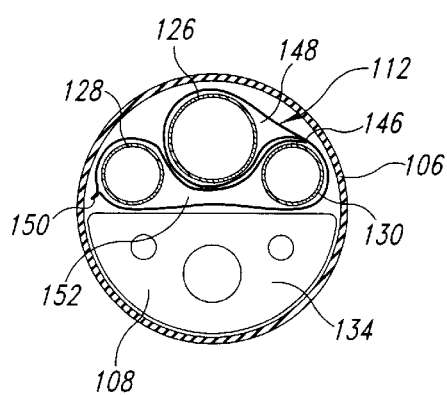
FIG. 5 is a cross-sectional view taken substantially along line 5—5 of FIG. 3 showing two lumens of the isolating sleeve with working channels extending through the lumens.

As best seen in FIG. 5, the biopsy channel 126 extends through the first lumen 148, and the water and air channels 128 and 130 extend through the second lumen 152 The isolating sleeve 112 is made of a material that has a low coefficient of friction between the material and each of the working channels 110, the endoscope tube 108, and the insertion tube 106. Accordingly, the isolating sleeve 112 reduces frictional resistance to articulation of the insertion tube 108.

In the preferred embodiment, the coefficient of friction between the isolating sleeve 112 and any of the working channels 110 is less than the coefficient of friction that would occur between the working channels if the isolating sleeve were not provided. The coefficient of friction between the isolating sleeve 112 and either of the endoscope tube 106 or the insertion tube 108 is also lower than the coefficient of friction between the working channels 110 and either of the endoscope tube or the insertion tube without the sleeve in place.

The first and second lumens 148 and 152 also prevent the working channels from tangling or twisting during installation of the endoscope and during an endoscopic procedure. The isolating sleeve 112 also retains the working channels 110 adjacent to the flat side of the insertion tube 108 during and after installation of the endoscope 102 into the sheath assembly 100.

In the preferred embodiment, the isolating sleeve 112 is elastically stretchable and allows for longitudinal elongation of the isolating sleeve as the articulating portion 134 of the insertion tube 108 is articulated about its neutral bending plane. During manufacturing of the isolating sleeve 112, the first and second lines of stitching 146 and 150 are sewn so they will stretch with the fabric upon articulation of the insertion tube 108. The preferred fabric is an elastic fabric, although alternate fabrics, such as microcoiled fabric or a wrinkled fiber fabric that are known in the textiles industry, may be used. In the preferred embodiment, the materials used are such that manufacturing of the sheath assembly is accomplished at a low cost, so it is economically feasible to dispose of the endoscope sheath assembly in a suitable receptacle after a single use.

In an alternate embodiment of the present invention, the isolating sleeve 112 is made from a low-friction material that is not elastically stretchable. This nonstretching isolating sleeve 112 has a length greater than the length of the working channels 110 extending through the isolating sleeve when the working channels 110 and the insertion tube 108 are straight. Accordingly, the nonstretching isolating sleeve 112 is slightly bunched when the working channels 110 are straight.

The length of the nonstretching isolating sleeve 112 is sufficient to allow the material to be moved approximately to its full length upon full articulation of the insertion tube 108 in the direction which causes elongation of the working channels, e.g., when the insertion tube 108 is articulated to move the distal end 122 downwardly. When the insertion tube 108 is articulated in the opposite direction, e.g., to move the insertion tube's distal end 122 upwardly resulting in contraction of the working channels 110, the isolating sleeve 112 bunches up. Although the nonstretching isolating sleeve 112 bunches within the endoscope tube 108, such bunching does not restrict articulation of the insertion tube 110.

Figure 6:
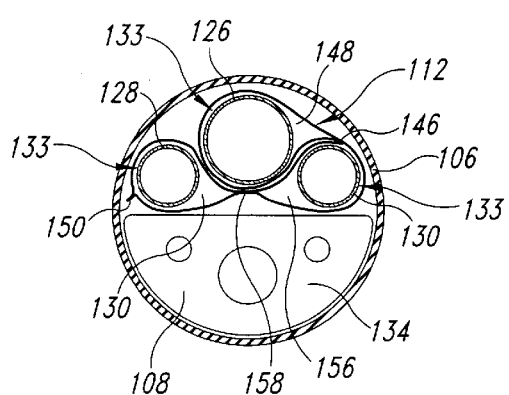
FIG. 6 is a cross-sectional view of an alternative embodiment of the endoscopic sheath assembly wherein the isolating sleeve has three sleeve lumens formed therein.

In an alternate embodiment illustrated in FIG. 6, the isolating sleeve 112 has a third lumen 156 formed by a third longitudinal line of stitching 158 extending substantially parallel to the first and second lines of stitching 146 and 150. In this alternate embodiment the third lumen 156 receives and isolates the air channel 130, the second lumen 152 receives and isolates the water channel 128, and the first lumen 148 receives and isolates the biopsy channel 126. Accordingly, the distal portions 133 of each working channel 110 are isolated from each, from the endoscope tube 106, and the insertion tube 108.

Testing has shown up to a 20% reduction in articulating force required to fully articulate the insertion tube 108 and sheath assembly 100 of the present invention at the articulating section 134. Such reduction in the articulation force translates into reduced operator fatigue and a feel that is closer to that of a conventional non-sheathed endoscope while maintaining the benefits of the sheathed endoscope. The insertion tube 108 of the endoscope 102 is also able to be more flexible because the bending resistance of the sheath assembly 100 is significantly reduced, and in some cases by over 50%, from a conventional sheath assembly that does not include the isolating sleeve 112.

From the foregoing it will be appreciated that specific embodiments of the invention have been described herein for purposes of illustration. Numerous modifications and variations of the endoscopic sheath assembly in accordance with the present invention will be apparent to those skilled in the art in view of the present disclosure. For example, the isolating sleeve 112 may extend along the full length of the working channels 110 within the endoscope tube 106. Therefore, it is to be understood that these modifications and variations, and equivalents thereof may be practiced while remaining within the spirit and scope of the invention as defined in the following claims.

We claim:

1. An endoscope sheath assembly usable with an elongated, flexible endoscope having an articulatable insertion tube, the assembly comprising:

an endoscope sheath having an endoscope tube having an open proximal end for receiving the endoscope insertion tube and closed distal end, the endoscope tube adapted to isolate at least a portion of the insertion tube from an external environment when the insertion tube is positioned within the endoscope tube;

first and second working channels extending through a portion of the endoscope tube and terminating adjacent to the closed distal end of the endoscope tube, the first and second working channels being positionable generally adjacent to the insertion tube when the insertion tube is within the endoscope sheath; and an isolating sleeve positioned in the endoscope tube and surrounding a portion of each of the first and second working channels to isolate the first and second working channels from the endoscope tube, the isolating sleeve having first and second sleeve lumens formed therein, a portion of the first working channel extending through the first sleeve lumen and a portion of the second working channel extending through the second sleeve lumen, the first and second working channels each being axially movable within the respective first and second sleeve lumens relative to each other upon articulation of the insertion tube.

2. The endoscope sheath assembly of claim 1 wherein the isolating sleeve has a distal end securely fixed to the distal end of the endoscope sheath and a proximal end securely fixed to the first and second working channels at a position proximal to the distal end of the endoscope sheath.

3. The endoscope sheath assembly of claim 1 wherein the isolating sleeve is a fabric material.

4. The endoscope sheath assembly of claim 3, wherein the fabric material is stretchable longitudinally.

5. The endoscope sheath assembly of claim 1 wherein the isolating sleeve is a sheet of material folded over onto itself and a joined together by lines of stitching along the length of the sheet to form the first and second sleeve lumens.

6. The endoscope sheath assembly of claim 5 wherein the sheet of material is a sheer, fabric material that is elastically stretchable and contractible longitudinally, and the lines of stitching are adapted to allow the sheet of material to stretch and contract longitudinally.

7. The endoscope sheath assembly of claim 1, further including a third working channel extending through the first sleeve lumen adjacent to the first working channel.

8. The endoscope sheath assembly of claim 1, further including a third working channel adjacent to the first and second working channels, and the isolating sleeve has a third sleeve lumen adjacent to the first and second lumens, the third working channel extending through the third sleeve lumen and being separated from the portions of the first and second working channels within the respective first and second sleeve lumens.

9. An endoscope sheath assembly usable with an elongated, flexible endoscope having an articulatable insertion tube, the assembly comprising:

an endoscope sheath having a flexible endoscope tube;

first and second working channels extending through a portion of the endoscope tube; and an isolating sleeve positioned in the endoscope tube and surrounding a portion of each of the first and second working channels to isolate the first and second working channels from the endoscope tube, the isolating sleeve having a lumen formed therein, portions of the first and second working channels extending through the lumen, the first and second working channels each being axially movable within the lumen relative to the endoscope sheath upon articulation of the insertion tube, the isolating sleeve having a distal end securely fixed to a distal end of the endoscope sheath and a proximal end securely fixed to the first and second working channels at a position proximal to the distal end of the endoscope sheath.

10. An endoscope sheath assembly usable with an elongated, flexible endoscope having an articulatable insertion tube, the assembly comprising:

an endoscope sheath having a flexible endoscope tube;

first and second working channels extending through a portion of the endoscope tube; and an isolating sleeve positioned in the endoscope tube and surrounding a portion of each of the first and second working channels to isolate the first and second working channels from the endoscope tube, the isolating sleeve having a lumen formed therein, portions of the first and second working channels extending through the lumen, the first and second working channels each being axially movable within the lumen relative to the endoscope sheath upon articulation of the insertion tube, the isolating sleeve being stretchable longitudinally.

11. An endoscope sheath assembly usable with an elongated, flexible endoscope having an articulatable insertion tube, the assembly comprising:

an endoscope sheath having a flexible endoscope tube;

first and second working channels extending through a portion of the endoscope tube; and an isolating sleeve positioned in the endoscope tube and surrounding a portion of each of the first and second working channels to isolate the first and second working channels from the endoscope tube, the isolating sleeve having a lumen formed therein, portions of the first and second working channels extending through the lumen, the first and second working channels each being axially movable within the lumen relative to the endoscope sheath upon articulation of the insertion tube, the isolating sleeve being sheet of material folded over onto itself and a joined together by a line of stitching to form the lumen.

12. A sheathed endoscope assembly, comprising:

an endoscope having an articulatable insertion tube having proximal and distal ends;

an endoscope sheath removably attached to the endoscope, the endoscope sheath having an opening at said proximal end for receiving the insertion tube and a closed distal end positioned adjacent to the distal end of the insertion tube, the endoscope sheath having a flexible endoscope tube surrounding the insertion tube and isolating the insertion tube from an external environment;

first and second of working channels extending through a portion of the endoscope tube and terminating adjacent to the closed distal end of the endoscope tube; and an isolating sleeve positioned in the endoscope tube and surrounding portions of the first and second working channels, the isolating sleeve having first and second lumens extending therethrough, a portion of the first working channel extending through the first lumen and a portion of the second working channel extending through the second lumen, the first and second working channels each being longitudinally movable within the respective first and second lumens relative to the endoscope tube upon articulation of the insertion tube.

13. The sheathed endoscope assembly of claim 12 wherein the isolating sleeve has a distal end securely fixed to the distal end of the endoscope sheath and a proximal end securely fixed to the first and second working channels at a position proximal to the distal end of the endoscope sheath.

14. The sheathed endoscope assembly of claim 12 wherein the isolating sleeve is a longitudinally stretchable fabric material.

15. The sheathed endoscope assembly of claim 12 wherein the isolating sleeve is made of a first material, the first working channel being made of a second material, and the second working channel being made of a third material, the first material engaging one of the second and third materials with a first coefficient of friction therebetween, the first coefficient of friction being less than a second coefficient of friction between the second and third materials.

16. The sheathed endoscope assembly of claim 15 wherein the first material is a fabric material.

17. The sheathed endoscope assembly of claim 12 wherein the isolating sleeve is a sheet of material folded over onto itself and a joined together by lines of stitching to form the first and second sleeve lumens.

18. The sheathed endoscope assembly of claim 12, further including a third working channel extending through the first sleeve lumen adjacent to the first working channel.

19. The sheathed endoscope assembly of claim 12, further including a third working channel extending through the endoscope tube generally adjacent to the first and second working channels, and the isolating sleeve has a third lumen therein adjacent to the first and second lumens, a portion of the third working channel extending through the third sleeve lumen and being longitudinally movable within the third lumen relative to the first and second working channels.

20. A endoscope sheath assembly usable with an elongated, flexible endoscope having an articulatable insertion tube, comprising:

a sheath means for isolating at least a portion of the insertion tube from an external environment, the sheath means having a flexible endoscope tube sized to removably receive the insertion tube;

first and second fluid carrying means for carrying fluid through the endoscope tube; and an isolating means within the endoscope tube having first and second lumens formed therein, the first lumen surrounding the first fluid carrying means and the second lumen surrounding the second fluid carrying means to isolate the first and second fluid carrying means from the endoscope tube, the first and second fluid carrying means each being axially movable within the respective first and second lumens relative to each other upon articulation of the insertion tube.

21. The endoscope sheath assembly of claim 20 wherein the isolating means has a distal end securely fixed to a distal end of the sheath means and a proximal end securely fixed to the first and second fluid carrying means at a position proximal to the distal end of the sheath means.

22. The endoscope sheath assembly of claim 20 wherein the isolating means is a fabric isolating sleeve.

23. The endoscope sheath assembly of claim 20 wherein the isolating means is a sheet of fabric material folded over onto itself and joined together to form the first and second lumens.

24. A method of isolating working channels of an endoscopic sheath assembly from an insertion tube of an endoscope installed in the sheath assembly, comprising the steps of:

positioning first and second working channels within an endoscope tube of the endoscopic sheath assembly;

enclosing a distal portion of the first working channel in a lumen of a first sleeve portion with the first sleeve portion being within the endoscope tube, the first sleeve portion isolating the distal portion of the first working channel from the endoscope tube; and enclosing a distal portion of the second working channel in a lumen of a second sleeve portion with the second sleeve portion being within the endoscope tube, the second sleeve portion isolating the distal portion of the second working channel from the endoscope tube and the first working channel.

25. The method of claim 24, further comprising the step of inserting an insertion tube of the endoscope into the interior area of the endoscope tube with a portion of the insertion tube being adjacent to the first and second distal portions of the first and second working channels, and the step of enclosing the first distal portion includes isolating with the first sleeve portion the first distal portion of the first working channel from the insertion tube.

26. The method of claim 24, further comprising the steps of positioning a third working channel within the interior area of the endoscope tube, and enclosing a third distal portion of the third working channel in the lumen of the first sleeve portion.

27. The method of claim 24, further comprising the steps of positioning a third working channel within the interior area of the endoscope tube, and enclosing a third distal portion of the third working channel in a lumen of a third sleeve portion.

28. A method of articulating an insertion tube of an endoscope and a sheath assembly connected to the insertion tube, comprising the steps of:

inserting the insertion tube into an endoscopic sheath assembly with the insertion tube being isolated from an external environment by an endoscope tube of the endoscopic sheath assembly, the sheath assembly having first and second working channels extending through the endoscope tube;

enclosing a distal portion of the first working channel in a first sleeve and isolating the distal portion of the first working channel from the insertion tube and the endoscope tube;

enclosing a distal portion of the second working channel in a second sleeve and isolating the distal portion of the second working channel from the distal portion of the first working channel; and articulating a distal portion of the insertion tube and the distal portions of the first and second working channels about a neutral bending plane spaced apart from the first and second working channels.

29. The method of claim 28, further including the step of moving the distal portions of the first and second working channels axially within the respective first and second sleeve as the distal portion of the insertion tube is articulated about the neutral bending plane.

* * * * *